United States Patent
Whittaker et al.

(10) Patent No.: US 10,675,448 B2
(45) Date of Patent: Jun. 9, 2020

(54) GUIDEWIRE CONTROL DEVICE

(75) Inventors: David R. Whittaker, Potomac, MD (US); Ryan S. Klatte, Fairview Park, OH (US); Shawn D. Ellis, Golden Valley, MN (US); Jason T. Mikulski, Bloomington, MN (US)

(73) Assignees: PARKER-HANNIFIN CORPORATION, Cleveland, OH (US); WINDCREST LLC, Potomac, MD (US); THE CLEVELAND CLINIC FOUNDATION, Cleveland, OH (US)

( * ) Notice: Subject to any disclaimer, the term of this patent is extended or adjusted under 35 U.S.C. 154(b) by 2599 days.

(21) Appl. No.: 13/157,627

(22) Filed: Jun. 10, 2011

(65) Prior Publication Data

US 2011/0306900 A1 Dec. 15, 2011

Related U.S. Application Data

(60) Provisional application No. 61/353,390, filed on Jun. 10, 2010.

(51) Int. Cl.
*A61M 25/09* (2006.01)

(52) U.S. Cl.
CPC ............ *A61M 25/09041* (2013.01); *A61M 2025/09116* (2013.01)

(58) Field of Classification Search
CPC ........ A61B 5/6851; A61B 2017/22049; A61B 2017/22047; A61M 25/09; A61M 25/09041; A61M 2025/09; A61M 2025/09125; A61M 2025/09116

USPC ................................. 600/585, 433–435, 528
See application file for complete search history.

(56) References Cited

U.S. PATENT DOCUMENTS

| | | | |
|---|---|---|---|
| 4,034,882 A * | 7/1977 | Wright | ................. B65D 50/043 |
| | | | 215/217 |
| 4,157,674 A * | 6/1979 | Carlson et al. | ............... 411/389 |
| 5,137,288 A | 8/1992 | Starkey et al. | |
| 5,161,534 A | 11/1992 | Berthiaume | |
| 5,224,939 A * | 7/1993 | Holman et al. | ............... 604/528 |
| 5,238,005 A | 8/1993 | Imran | |
| 5,392,778 A | 2/1995 | Horzewski | |
| 5,415,633 A | 5/1995 | Lazarus et al. | |
| 5,443,078 A | 8/1995 | Uflacker | |
| 5,480,382 A | 1/1996 | Hammerslag et al. | |

(Continued)

FOREIGN PATENT DOCUMENTS

EP   0 310 295 A2   4/1989
EP   0 383 914 A1   8/1990

(Continued)

*Primary Examiner* — Devin B Henson
*Assistant Examiner* — Huong Q Nguyen
(74) *Attorney, Agent, or Firm* — Tarolli, Sundheim, Covell & Tummino LLP

(57) ABSTRACT

A controller (10) for manually controlling a guidewire (50) includes a housing (100) including a passage (112) for receiving the guidewire. A gripper (140) is actuatable to grasp the guidewire (50) in the passage (112). A cap (200) is connected to the housing (100). The cap (200) is rotatable relative to the housing (100) to actuate the gripper (140). The housing (100) includes an element (160) for maintaining the cap (200) in a receiving position. The cap (200) when in the receiving position places the controller (10) in a condition for receiving the guidewire (50).

29 Claims, 6 Drawing Sheets

(56) References Cited

U.S. PATENT DOCUMENTS

| | | | |
|---|---|---|---|
| 5,492,131 A | 2/1996 | Galel | |
| 5,636,642 A | 6/1997 | Palermo | |
| 5,771,902 A | 6/1998 | Lee et al. | |
| 5,851,189 A | 12/1998 | Forber | |
| 5,906,590 A | 5/1999 | Hunjan et al. | |
| 5,916,147 A | 6/1999 | Boury | |
| 6,033,414 A | 3/2000 | Tockman et al. | |
| 6,231,563 B1 | 5/2001 | White et al. | |
| 6,352,515 B1 | 3/2002 | Anderson et al. | |
| 6,500,130 B2 | 12/2002 | Kinsella et al. | |
| 6,502,606 B2 | 1/2003 | Klint | |
| 6,514,237 B1 | 2/2003 | Maseda | |
| 6,533,772 B1 | 3/2003 | Sherts et al. | |
| 6,551,302 B1 | 4/2003 | Rosinko et al. | |
| 6,579,246 B2 | 6/2003 | Jacobsen et al. | |
| 6,579,279 B1 | 6/2003 | Rabiner et al. | |
| 6,616,628 B2 | 9/2003 | Hayzelden | |
| 6,714,809 B2 | 3/2004 | Lee et al. | |
| 7,615,032 B2 | 11/2009 | Whittaker et al. | |
| 8,038,628 B2 * | 10/2011 | von Malmborg et al. | ... 600/585 |
| 2001/0039412 A1 | 11/2001 | Fariabi | |
| 2002/0013550 A1 | 1/2002 | Unsworth et al. | |
| 2002/0072689 A1 | 6/2002 | Klint | |
| 2002/0082523 A1 | 6/2002 | Kinsella et al. | |
| 2003/0078645 A1 | 4/2003 | Pigott | |
| 2003/0097080 A1 | 5/2003 | Esashi et al. | |
| 2003/0181827 A1 | 9/2003 | Hojeibane et al. | |
| 2003/0199818 A1 | 10/2003 | Waldhauser et al. | |
| 2003/0208219 A1 | 11/2003 | Aznoian et al. | |
| 2004/0039250 A1 | 2/2004 | Tholfsen et al. | |
| 2004/0133185 A1 | 7/2004 | Nash et al. | |
| 2007/0179472 A1 | 8/2007 | Whittaker et al. | |
| 2008/0294030 A1 * | 11/2008 | von Malmborg et al. | ... 600/374 |
| 2008/0319345 A1 * | 12/2008 | Swenson | ... 600/576 |
| 2009/0198153 A1 | 8/2009 | Shriver | |
| 2010/0234897 A1 * | 9/2010 | Fisher et al. | ... 606/286 |

FOREIGN PATENT DOCUMENTS

| | | |
|---|---|---|
| EP | 0 543 539 A1 | 5/1993 |
| JP | 1 198564 A | 8/1989 |
| JP | 5 177002 A | 7/1993 |
| WO | WO-1990/003760 A1 | 4/1990 |
| WO | WO-1993/002567 A1 | 12/1993 |
| WO | WO-1996/013206 A1 | 5/1996 |
| WO | WO-2002/083010 A1 | 10/2002 |
| WO | WO-2004/000107 A2 | 12/2004 |
| WO | WO-2005/094935 A1 | 10/2005 |
| WO | WO-2005/094936 A2 | 10/2005 |
| WO | WO-2005/094937 A1 | 10/2005 |
| WO | WO-2010/045373 A1 | 4/2010 |

\* cited by examiner

GUIDEWIRE CONTROL DEVICE

RELATED APPLICATIONS

This application claims the benefit of U.S. Provisional Application Ser. No. 61/353,390, filed on Jun. 10, 2010.

TECHNICAL FIELD

The present invention relates to the medical field, specifically to such devices used for the interventional and diagnostic access, manipulation within and negotiation of the vascular system.

BACKGROUND OF THE INVENTION

The vascular field of medicine relates to the diagnosis, management and treatment of diseases effecting the arteries and veins. The normal anatomy of these vessels is complex—with numerous divisions leading into progressively smaller branches. The development of disease within these vessels often alters their caliber, flexibility, and direction. These vessel's lumens will frequently become severely stenotic and at times, obstructed, by the development of atherosclerotic plaques or dissections. These obstructions may lead to the formation of new collateral pathways that follow new routes around the obstructions to provide blood flow down-stream from the blockage.

In order to diagnose and treat many vascular diseases, it is necessary for a physician to perform a diagnostic or interventional angiogram. Angiograms are specialized X-rays requiring access into a vessel with some form of sheath, needle or guide that allows contrast dye to be injected into the vasculature while X-rays are obtained. The contrast dye illuminates the interior of the vessels and allows the physician to note the anatomy as well as narrowings, abnormalities and blockages within the vessels. At times, more selective angiograms are necessary to better delineate a particular area of concern or disease. In order to obtain access to these more selective areas, it is necessary to insert guidewires and guide catheters into the vessels.

These devices can be visualized externally by the use of continuous low-dose fluoroscopy as they are manipulated through the body's vascular system. Even in conditions of normal anatomy, the negotiation of this rather complex anatomy can be difficult, time-consuming and frustrating. With the addition of diseased vessels that are narrowed or obstructed, such negotiation is significantly more difficult, and at times, impossible.

In an attempt to improve the situation, there have been a multitude of guidewires designed to negotiate these complex anatomies. Several different guidewire designs exist, each with a variation in its shape, size or length. In order to negotiate the smaller blood vessels as well as to provide some standardization within the industry, most catheterization systems work with guidewire diameters of 0.035" or less. (0.018" and 0.014" being the next most common sizes, but sizes extend down to as small as 0.010")

All of these guidewires are manipulated through the vascular anatomy via a combination of axial and rotational movements. Most guidewires have a tip that is bent, shaped or biased off the centerline. As the guidewire is advanced through the vasculature, it can be rotated to orient its tip in a different direction to facilitate its movement through the complex anatomy.

Since these guidewires all have small diameters, a gloved user will often have difficulty successfully gripping the guidewire to facilitate the necessary movements. Additionally, many guidewires have surface coatings designed to decrease the coefficient of friction and make the guidewires more slippery. This further contributes to the difficulty of controlling these guidewires.

In order to improve the control of these guidewires, many types of control devices have been developed. These are often referred to as Controllers or Torquers. They typically consist of a gripping mechanism that can be temporarily attached to the guidewire and a body attached to the gripping mechanism that can be gripped by the user. The gripping mechanism and the body provide the user with a better grasp of the guidewire and often provide a mechanical advantage to improve the provider's ability to move the guidewire.

The vast majority of these control devices are placed on the guidewire by co-axially loading the device on the guidewire at its most proximal end and sliding the device along the wire until it is at the place of use by the provider. When the device is at the desired location, it then is activated by the user to grip the guidewire. As the guidewire is manipulated through the anatomy, the device can be repositioned by releasing the gripping mechanism and sliding the device along the guidewire. When the device is no longer required, it can be removed from the guidewire by sliding it axially off the guidewire from its proximal endpoint.

A problem with this typical end-loaded (also referred to as over-the-wire) type of design relates to the significant amount of moving contact with the guidewire. This excess amount of movement increases the possibility that the guidewire can be inadvertently moved resulting in loss of position, damage to a vessel or failure of a procedure. Additionally, this increased degree of motion creates wasted motion, increases procedure time and can increase user frustration.

SUMMARY OF THE INVENTION

The present invention relates to A controller for manually controlling a guidewire includes a housing including a passage for receiving the guidewire. A gripper is actuatable to grasp the guidewire in the passage. A cap is connected to the housing. The cap is rotatable relative to the housing to actuate the gripper. The housing includes an element for maintaining the cap in a receiving position. The cap when in the receiving position places the controller in a condition for receiving the guidewire.

The present invention also relates to a controller for manually controlling a guidewire. The controller includes a housing comprising a passage for receiving the guidewire. A gripper is actuatable to grasp the guidewire in the passage. A cap is connected to the housing and is rotatable relative to the housing to actuate the gripper. The cap has a threaded connection with the housing. The threads of at least one of the housing and cap have asymmetrical flank angles that facilitate an initial connection of the cap to the housing by inserting the housing axially into the cap without requiring rotation.

The present invention also relates to a controller for manually controlling a guidewire. The controller includes a housing comprising a passage for receiving the guidewire. A gripper is actuatable to grasp the guidewire in the passage. A cap connected to the housing is rotatable relative to the housing to actuate the gripper. The gripper includes collet fingers spaced asymmetrically about the passage so that a space between a first adjacent pair of fingers is greater than spaces between remaining adjacent pairs of fingers. The space between the first adjacent pair permits insertion of the guidewire between the first adjacent pair. The space between the remaining adjacent pairs helps position the guidewire in the passage until the gripper is actuated to grasp the guidewire.

The present invention also relates to a controller for manually controlling a guidewire. The controller includes a housing comprising a passage for receiving the guidewire. A gripper that is actuatable to grasp the guidewire in the passage. A cap connected to the housing is rotatable relative to the housing to actuate the gripper. The housing includes an element that blocks rotation of the cap to thereby prevent disconnection of the cap from the housing.

The present invention further relates to a controller for manually controlling a guidewire. The controller includes a housing including a passage for receiving the guidewire. A gripper is actuatable to grasp the guidewire in the passage. A cap connected to the housing is rotatable relative to the housing to actuate the gripper. The housing comprises an element that inhibits rotation of the cap at an adjusting position at which the axial position of the controller relative to the guidewire can be adjusted.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
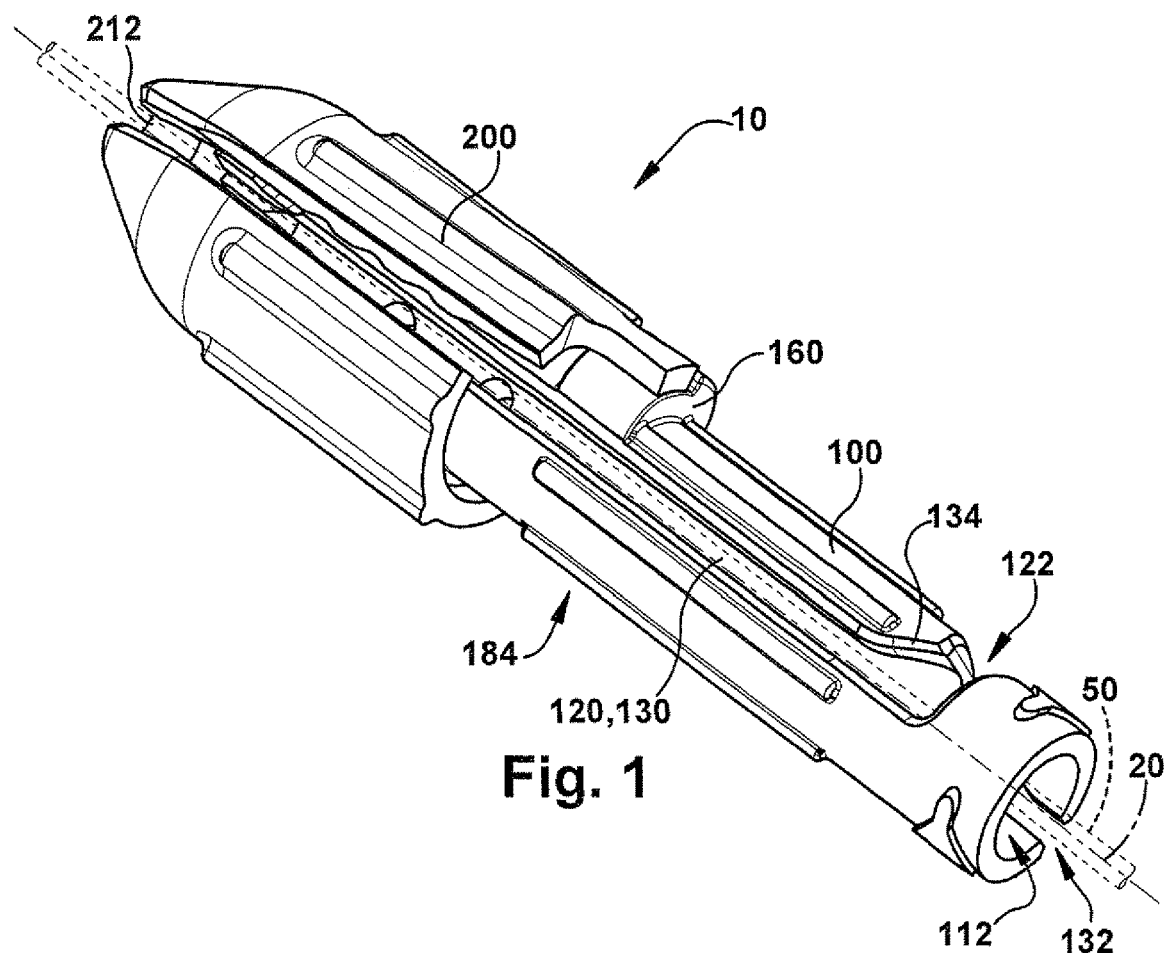
FIGS. 1 and 2 are perspective views of a guidewire control apparatus.
Figure 2:
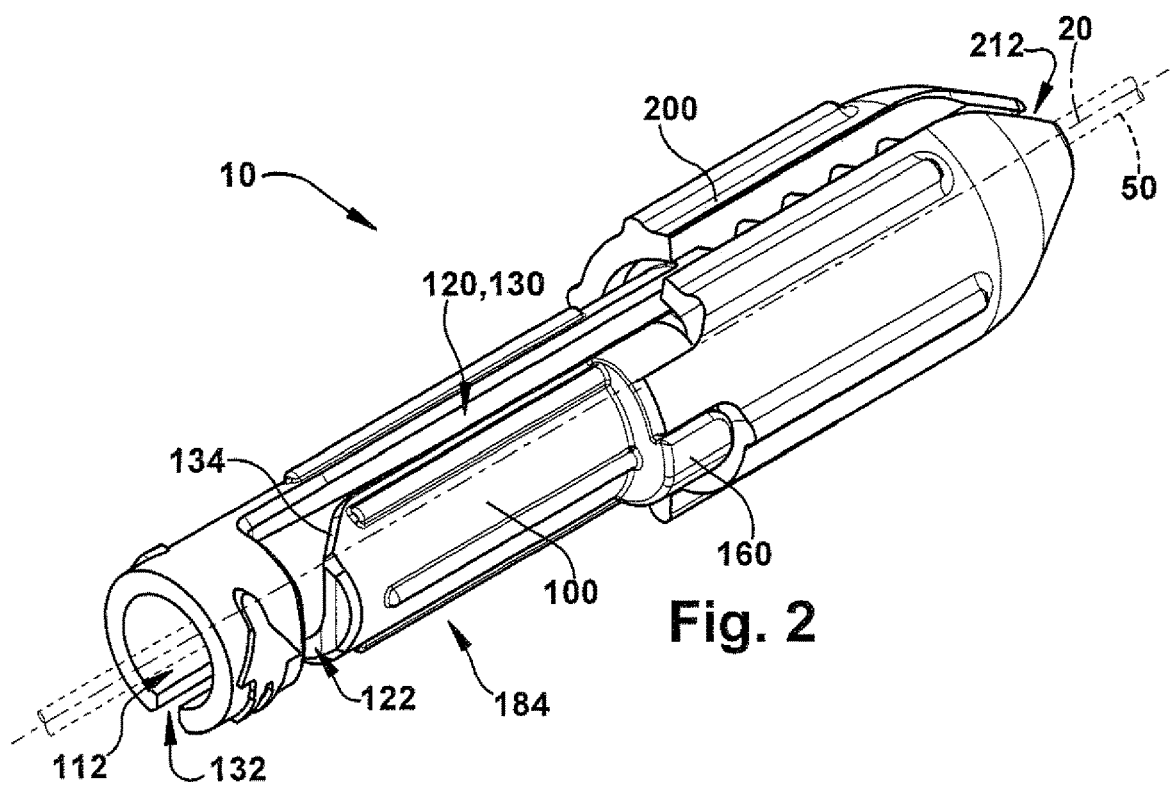

The present invention relates to an apparatus for controlling a guidewire, referred to herein as a controller. FIGS. 1 and 2 illustrate a controller 10 for controlling a guidewire 50 in accordance with the present invention. The controller 10 includes a housing 100 and a cap 200 that is connectable to the housing through a threaded engagement. The controller 10 has a central longitudinal axis 20 which the housing 100 and cap 200 share when assembled via the threaded connection, as shown in FIGS. 1 and 2. The axial and rotational position of the cap 200 on the housing 100 can be adjusted by rotating the cap about the axis 20 relative to the housing. The cap 200 can also be removed from the housing 100.

The housing 100 and cap 200 can be made of any material suited for medical purposes within recognized federal (e.g., FDA) and industry guidelines. In one particular example, the housing 100 and cap could be constructed of injection molded plastic. For instance, the housing 100 could be constructed of a polycarbonate resin material, such as Lexan® polycarbonate resin, which is commercially available from SABIC (Saudi Basic Industries Corporation) of Saudi Arabia, and formerly available from GE Plastics. The cap 200 could be constructed of a polyoxymethylene copolymer, such as Hostaform®, which is commercially available from Ticona Engineering Polymers, a unit of the Celanese Corporation of the United States of America. Those skilled in the art will appreciate that other suitable materials may be selected for one or both of the housing 100 and cap 200.

Figure 3:
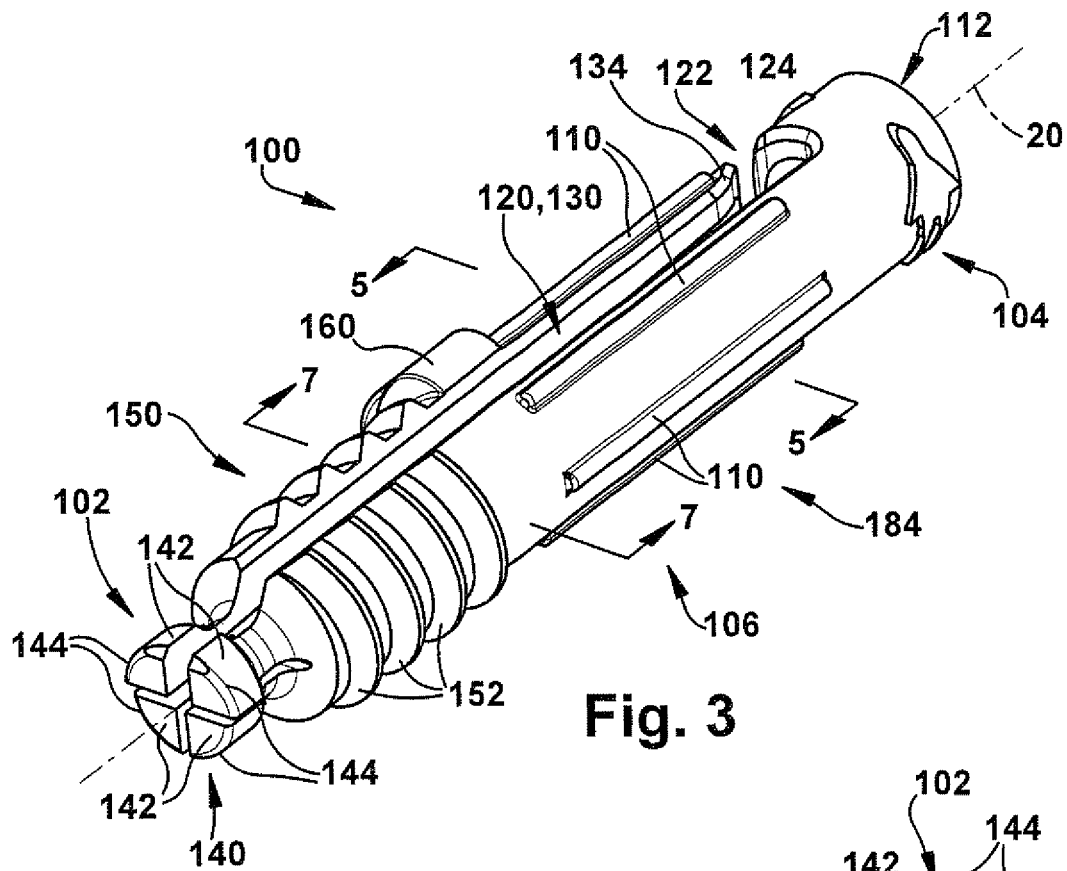
FIGS. 3 and 4 are perspective views of a portion of the control apparatus of FIGS. 1 and 2.
Figure 4:
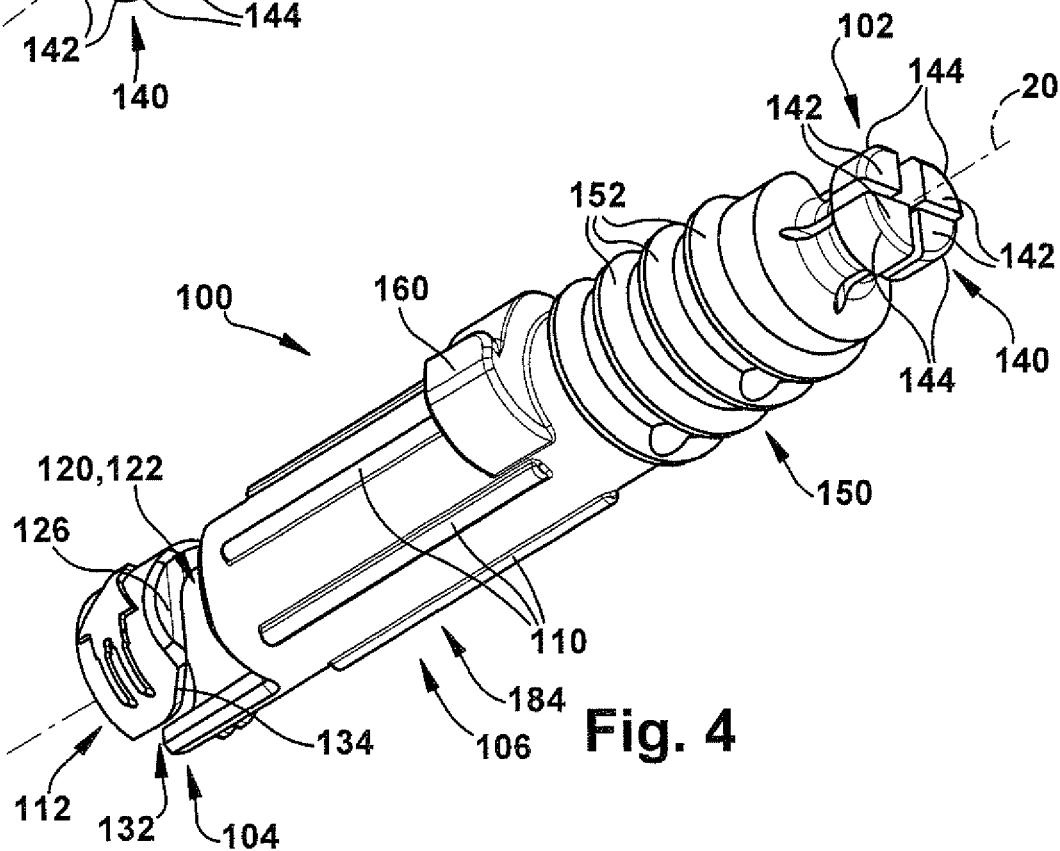
Figure 5:
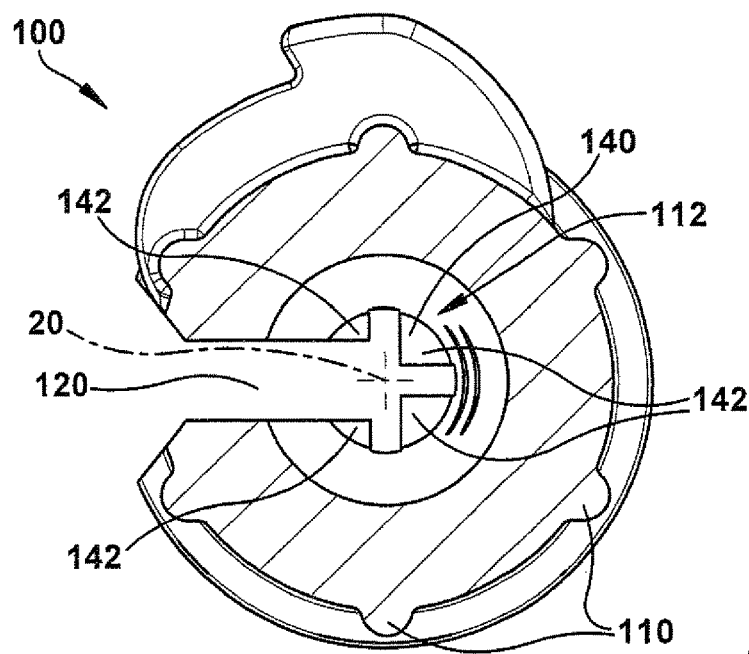
FIG. 5 is a sectional view taken generally along line 5-5 in FIG. 3.

Referring to FIGS. 3-5, the housing 100 has a first end portion 102 and an opposite second end portion 104. A central body portion 106 of the housing 100 may include ribs 110 that help facilitate gripping and maneuvering the controller 10. The housing 100 includes a central passage 112 that extends along the length of the housing from the first end portion 102 to the second end portion 104. The passage 112 is centered on the axis 20 and provides clear passage through the housing 100 along the axis. Referring to FIGS. 1-5, the guidewire 50, when received in the controller 10, is positioned in the passage 112 and extends in a substantially coaxial along the axis 20.

The housing 100 includes a slot 120 that intersects with and provides guidewire access to the passage 112 along the entire length of the passage. The slot 120 may have beveled edges so as to help guide the guidewire 50 into the slot and to help prevent damage to the guidewire during installation of the controller 10. The slot 120 includes an engagement portion 122 positioned at the second end 104 of the housing 100. The engagement portion 122 extends transverse to the axis 20 and has a first end 124 and an opposite second end 126. The slot 120 also includes a primary receiving portion 130 that extends axially along the housing 100 from the first end 102 of the housing along the central body portion 106 and intersects the first end 124 of the engagement portion 122. The slot 120 further includes a secondary receiving portion 132 that extends parallel to the axis 20 from the second end 104 of the housing 100 and intersects the second end 126 of the engagement portion 122.

The primary receiving portion 130 and the secondary receiving portion 132 are positioned on radially opposite sides of the housing 100. The engagement portion 122 extends transversely between and interconnects the primary receiving portion 130 to the secondary receiving portion 132. At the interface between the primary receiving portion 130 and the engagement portion 122, the housing may include a beveled portion 134. Similarly, at the interface between the secondary receiving portion 132 and the engagement portion 122, the housing may include a beveled portion 136. The beveled portions 134 and 136 may help prevent excessive bending or kinking of the guidewire 50 during installation.

Referring to FIGS. 3-5, the first end 102 of the housing 100 includes a gripper 140 for grasping the guidewire 50. The gripper 140 forms a terminal end of the housing 100. The gripper 140 comprises or takes the basic form of a collet, and includes a plurality of fingers 142 for applying a gripping force to the guidewire 50. In the illustrated embodiment, there are four such fingers 142. Those skilled in the art, however, will appreciate that the gripper 140 may include a greater number of fingers or fewer fingers. According to the present invention, the fingers 142 are spaced asymmetrically. Due to this asymmetrical spacing, the space between two of the fingers 142 is wider than the spacing between the remaining fingers and helps define the slot 120.

The fingers 142 of the gripper 140 are spaced about the axis 20 in a substantially equidistant manner. It should be noted, however, that the spacing between the fingers 142 that help define the slot 120 may be spaced from each other a slightly greater distance than that which exists between the other fingers to permit guidewire access through the slot. The remaining fingers 142 may be spaced so that the guidewire 50 cannot enter the space between them.

The fingers 142 are deflectable in radial directions with respect to the axis 20. In a normal and unbiased condition, which is illustrated in FIGS. 3-5, the fingers 142 are spaced from the axis a distance sufficient to permit the guidewire 50 to pass freely in the passage 112 between the fingers with little or no resistance. The fingers 142 are capable of being urged to converge toward the axis 20 into engagement with each other to block the passage 112.

Figure 6:
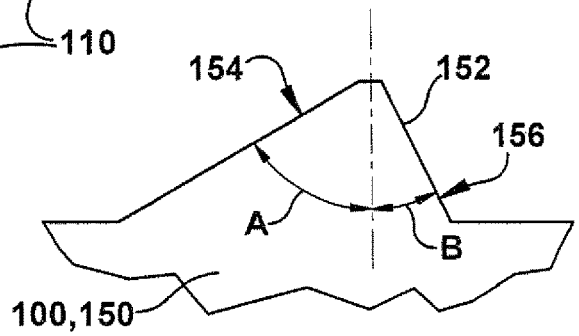
FIG. 6 is a magnified view of a portion of the control apparatus of FIGS. 3 and 4.

Adjacent the gripper 140 is a threaded portion 150 of the housing 100 that is adapted to cooperate with and receive the cap 200. The threaded portion 150 includes helical threads 152 that are illustrated in detail in FIG. 6. According to the present invention, the threads 152 are asymmetrical, i.e., the lead flank 154 has a flank angle, indicated generally at A in FIG. 6, that is greater than the flank angle of the rear flank 156, which is illustrated generally at B in FIG. 6.

Figure 7:
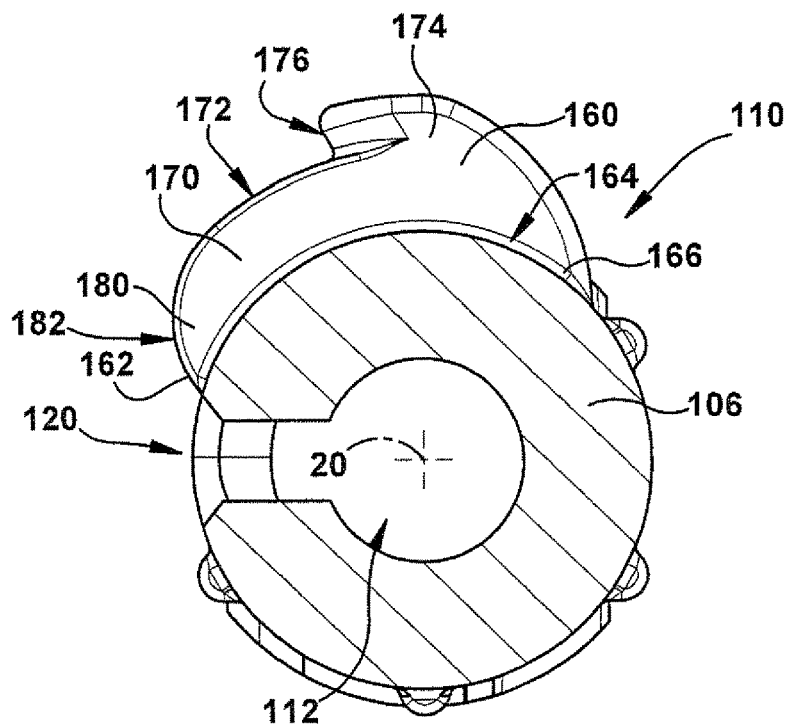
FIG. 7 is a sectional view taken generally along line 7-7 in FIG. 4.

Adjacent the threaded portion 150, the housing 100 includes a multi-function element 160 that projects outward from the central portion 106 of the housing away from the axis 20. FIG. 7 illustrates the element 160 in detail. The element 160 has a curved contour, merging at a first end 162 with the surface 164 of the central portion 106 adjacent the primary receiving portion 130 of the slot 120. An opposite second end 166 of the element 160 also terminates and merges with the outer surface 164, although at a larger or steeper angle than that at which the first end 162 merges.

The element 160 includes a first portion 170 that projects outward from the housing 100 and has an outward facing surface 172. The element 160 also includes a second portion 174, adjacent the first portion 170, that also projects outward from the housing 100. The second portion 174 projects further outward from the housing 100 than the first portion 170 and therefore has a height, as viewed in FIG. 7, that is greater than the height of the first portion. The second portion 174 has a lateral surface 176 formed where the element 160 transitions from the first portion 170 to the second portion 174. The lateral surface 176 of the second portion 174 extends transverse to the outward facing surface 172 of the first portion 170. The element 160 further includes a third portion 180 that is formed in the area of the first end portion 162 where the element merges with the outer surface 164. The third portion 180 includes a surface 182 that extends transverse to and merges with the outer surface 164.

Referring to FIGS. 1-5, adjacent the element 160, the central portion 106 of the housing portion comprises a gripping portion 184 of the controller 10. The gripping portion 184 provides an area at which the operator can grasp and maneuver the controller 10. The gripping portion 184 includes the ribs 110 to help facilitate this purpose.

Figure 8:
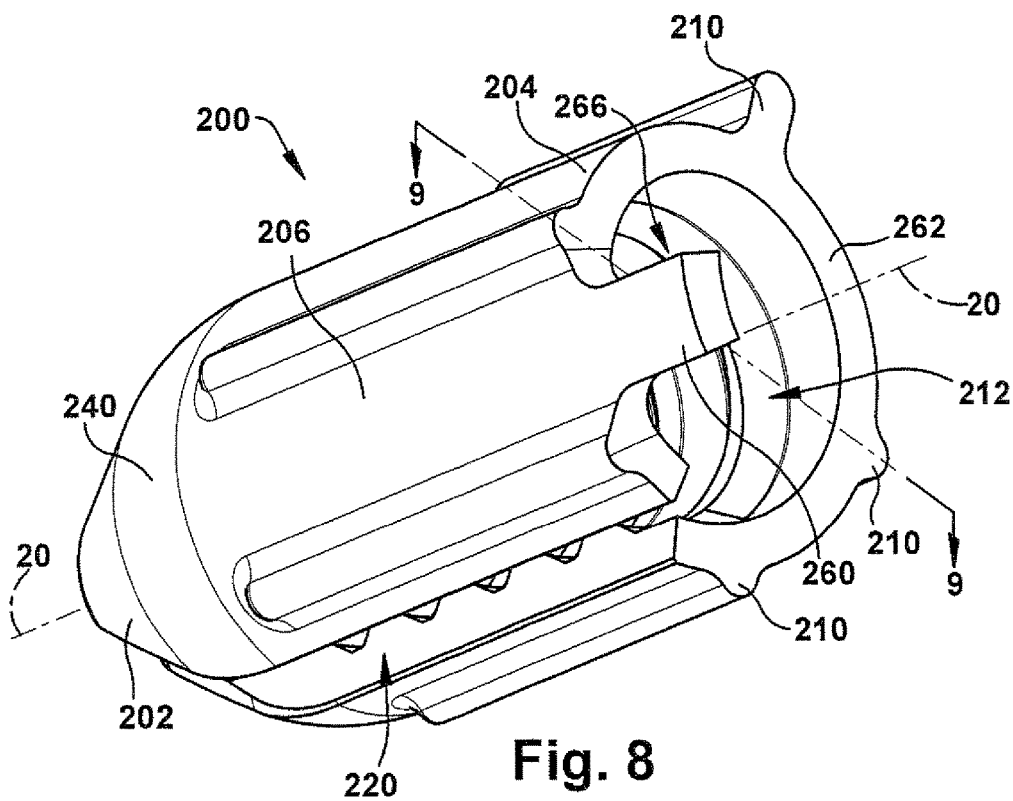
FIG. 8 is a perspective view of a portion of the control apparatus of FIGS. 1 and 2.
Figure 9:
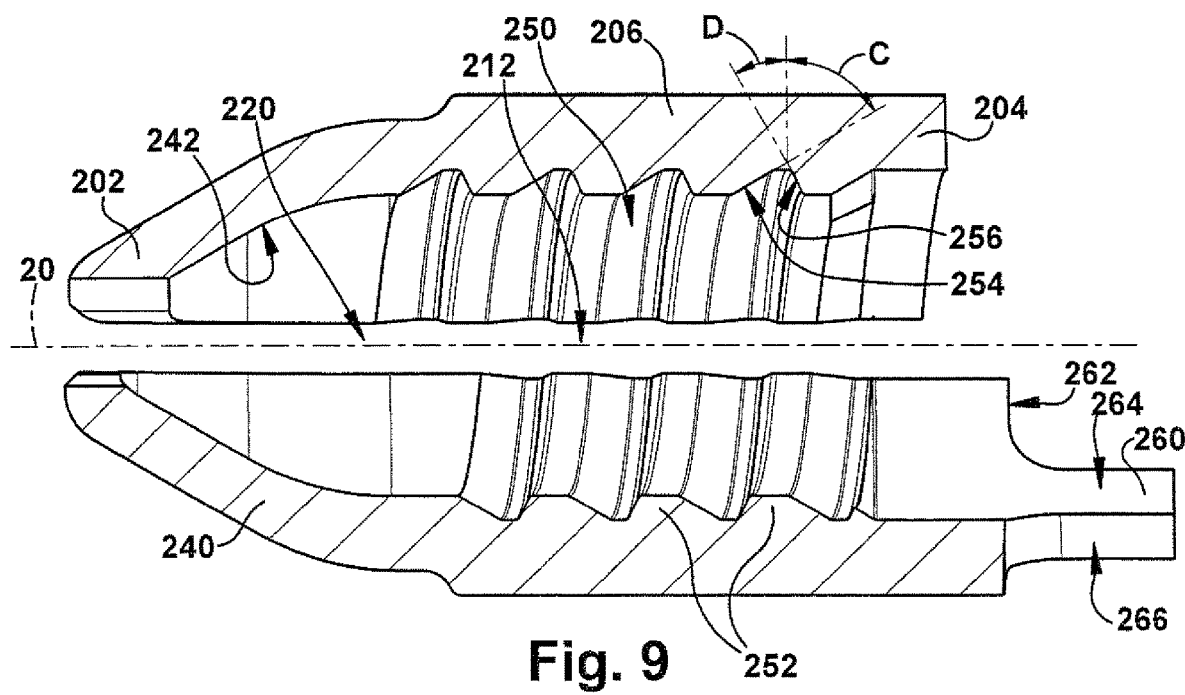
FIG. 9 is a sectional view taken generally along line 9-9 in FIG. 8.

Referring now to FIGS. 8 and 9, the cap 200 has a first end portion 202, an opposite second end portion 204, and a central portion 206 between the first and second end portions. The central body portion 206 of the cap 200 may include ribs 210 that help facilitate gripping and rotating the cap relative to the housing 100. The cap 200 includes a central passage 212 that extends along the length of the housing from the first end portion 202 to the second end portion 204. The passage 212 is centered on the axis 20 and provides clear passage through the cap 200 along the axis.

As shown in FIGS. 1 and 2, the passage 212 of the cap 200 and the passage 112 of the housing 100 coincide with each other and the guidewire 50, when received in the controller 10, is positioned in both passages 112 and 212, and extends in a substantially coaxial along the axis 20.

Referring to FIGS. 8 and 9, the cap 200 includes a slot 220 that intersects with and provides access to the passage 212 along the entire length of the passage. The slot 220 is linear in form and extends axially along the length of the cap 200 through the first end portion 202, through the central portion 206, and through the second end portion 204.

The first end portion 202 of the cap 200 has a tapered, generally conical, configuration. The first end portion comprises an actuator portion 240 designed to cooperate with the gripper 140 of the housing 100. More specifically, the actuator portion 240 of the cap 200 has an inner surface 242 that helps define the passage 212. The inner surface 242 acts as a reaction surface for engaging the fingers 142 of the gripper 140 during operation of the controller 10.

Adjacent the actuator portion 240 is a threaded portion 250 of the cap 200 that is adapted to cooperate with and receive the threaded portion 150 of the housing 100. The threaded portion 250 includes helical threads 252 that are illustrated in detail in FIG. 9. As shown in FIG. 9, the threads 252 may have a configuration designed to mate with and correspond to the threads 152 of the housing 100. Thus, similar or identical to the housing threads 152, the cap threads 252 may be asymmetrical, i.e., the lead flank 254 has a flank angle, indicated generally at C in FIG. 9, that is greater than the flank angle of the rear flank 256, which is illustrated generally at D in FIG. 9.

Adjacent the threaded portion 250 at the second end portion 204, the cap 200 includes a tab 260 that extends in a direction parallel to the axis 20 from a rear end surface 262 of the cap. The tab 260 has an inward facing surface 264 that faces generally toward the axis 20. The tab 260 also has a lateral surface 266 that faces in a generally tangential direction with respect to the outer diameter of the cap 200. The lateral surface 266 intersects the extends transverse to and intersects the inward facing surface 264. Owing to the construction of the cap 200, the tab 260 is deflectable in a radially outward direction with respect to the remainder of the cap.

Referring to FIGS. 1-5, adjacent the element 160, the central portion 106 of the housing portion comprises a gripping portion 184 of the controller 10. The gripping portion 184 provides an area at which the operator can grasp and maneuver the controller 10. The gripping portion 184 includes the ribs 110 to help facilitate this purpose.

To assemble the controller 10, the cap 200 is installed on the housing 100. This can be accomplished in one of two manners. First, the cap 200 can be screwed onto the housing 100 by rotating the cap and/or the housing to engage their respective housing threads 152 with the cap threads 252. Alternatively, according to the present invention, the asymmetrical form of the threads 152 and 252 allows the cap 200 to be installed on the housing 100 by urging the cap onto the housing with an axial motion that does not require rotation of either the cap or housing. The relatively large flank angles A and C, respectively, of the lead flanks 154 and 254 of the housing threads 152 and cap threads 252 permit the threaded portion 250 of the cap 200 to slide over the threaded portion 150 of the housing 100 with a clicking or snap on fit.

In doing so, the slot 212 in the cap 200 permits the threaded portion 250 to deflect radially due to the normal forces created when the lead flanks 154 and 254 of the housing 100 and cap 200, respectively, engage each other under the applied axial force. Since the flank angles A and C are comparatively large and measured normal to the axis 20, the lead flanks 154 and 254 have a low angle with respect to the axis 20. It is this low angle with respect to the axis 20 that causes the requisite normal forces to be generated with a comparatively low axial force applied between the cap 200 and housing 100. If this angle was too great, the requisite axial force could cause damage to one or both of the cap 200 and housing 100. This axial snap-fit functionality permits rapid assembly of the controller 10 during manufacturing.

Once assembled, the cap 200 can be rotated relative to the housing 100 to screw/unscrew the cap and thereby actuate the gripper 140. When the cap 200 is installed, the actuator portion 240 is positioned adjacent the gripper 140. In a non-actuated condition, the cap 200 is unscrewed to a position where the actuator portion 240 does not engage and deflect the fingers 142, and the fingers are therefore spaced apart under their own resilient characteristics as shown, for example, in FIGS. 3-5.

In an actuated condition, the cap 200 is screwed onto the housing 100 until the surface 242 of the actuator portion 240 engages the fingers 140. More specifically, the actuator portion 240 engages outer corner portions 144 of the fingers 142 where respective side surfaces meet respective end surfaces of the individual fingers. As the cap 200 is screwed further onto the housing 100, normal forces created by the tapered angle of the surface 242 of the actuator portion 240 urge the fingers to deflect converge toward the axis 20 in a gripping direction.

The asymmetrical spacing of the fingers 142 is advantageous because the guidewire 50, when inserted through the slot 120 and into the passage 112, will become seated against the two fingers 142 positioned opposite the slot. These fingers 142 will maintain the guidewire 50 positioned centered on the axis 20 until such a time that the cap 200 is tightened, thus actuating the gripper 140 to grasp the guidewire, as described above.

The cap 200 can be tightened until the fingers 142 engage each other, effectively closing the passage 112. Of course, with the presence of a guidewire 50 in the passage 112, the fingers 142 will be stopped prior to engaging each other due to the presence of the guidewire in the passage. In this actuated condition of the controller 10, the guidewire 50 is gripped, positioned coaxially with the axis 20, and can be maneuvered through manipulation of the controller.

The tab 260 of the cap 200 cooperates with the element 160 of the housing 100 to provide several functional features of the controller 10. The tab 260 and cap 200 provide tactile indication of various conditions of the controller 10, help block or prevent the controller from being placed in undesirable conditions, and help to maintain the controller in desired conditions.

Figure 11A:
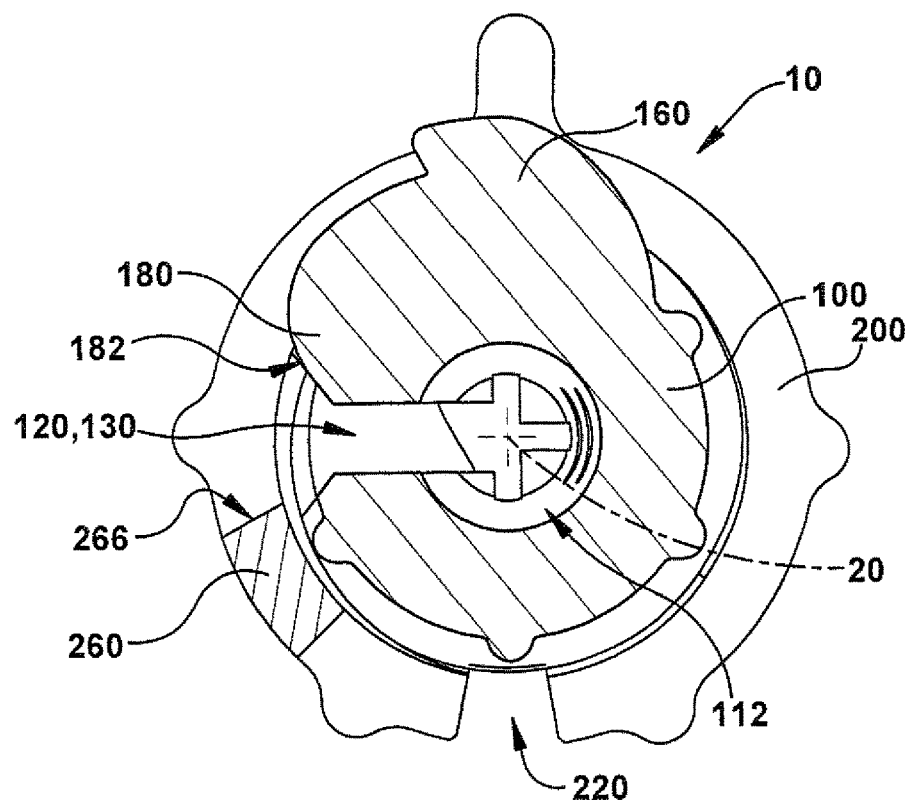
FIGS. 11A and 11B are sectional views illustrating the operation of certain portions of the control apparatus of FIGS. 1 and 2.

In a receiving condition of the controller 10, the tab 260 cooperates with the element 160 to help maintain the cap 200 in a receiving position that places the controller in a condition for receiving the guidewire 50. This is illustrated in FIG. 11A. Referring to FIG. 11A, when the cap 200 is in the receiving condition, the slot 212 of the cap is aligned with the slot 120 in the housing 100. Those skilled in the art will appreciate that it is both necessary and desirable to maintain the controller in the receiving condition during installation of the guidewire 50 to help ease the installation process and to help prevent any damage to the guidewire that otherwise may occur. Additionally, the receiving position of the controller 10 allows the controller to be removed from the guidewire 50 at any time and at any position along the length of the guidewire.

According to the present invention, as the cap 200 is rotated relative to the housing 100, the tab 260 approaches the element 160. When the tab 260 reaches the element 160, the tab slides onto the first end 162 of the element 160 and begins to slide onto the first portion 170. As this occurs, the first portion 170 causes the tab 260 to deflect radially outward with respect to the axis 20. When the cap 200 reaches the receiving position, the tab 260 is deflected through the engagement of the surface 264 with the surface 172 of the first portion 170 of the element 160. This engagement creates friction, which maintains the cap 200 in the receiving position, which allows the user to maneuver the controller 10 onto or off of the guidewire 50 without regard to maintaining the position of the cap.

Additionally, while the controller 10 is in the receiving condition, the tab 260 cooperates with the element 160 to block the cap 200 from being removed from the housing 100. This occurs when the lateral surface 266 of the tab 260 engages the lateral surface 176 of the second portion 174 and thereby prevents further rotation of the cap 200 relative to the housing 100 in the unscrewing/disconnecting direction.

Blocking rotation of the cap in the manner described above has several advantages. Since placing the controller 10 in the receiving position requires rotating the cap 200 in the direction of unscrewing the cap from the housing 100, those skilled in the art will appreciate that it may be desirable to block further rotation of the cap so as to prevent unwanted disconnection of the cap from the housing. Additionally, blocking rotation of the cap 200 at the receiving position also conveniently provides a tactile indication to the user that the controller 10 has been placed in the receiving condition. If, however, disconnection of the cap 200 from the housing 100 is desired, the user can manually deflect the tab 260 to move above the lateral surface 176 and over the second portion 174 of the element 160 to thereby allow further rotation of the cap in the unscrewing direction.

Figure 11B:
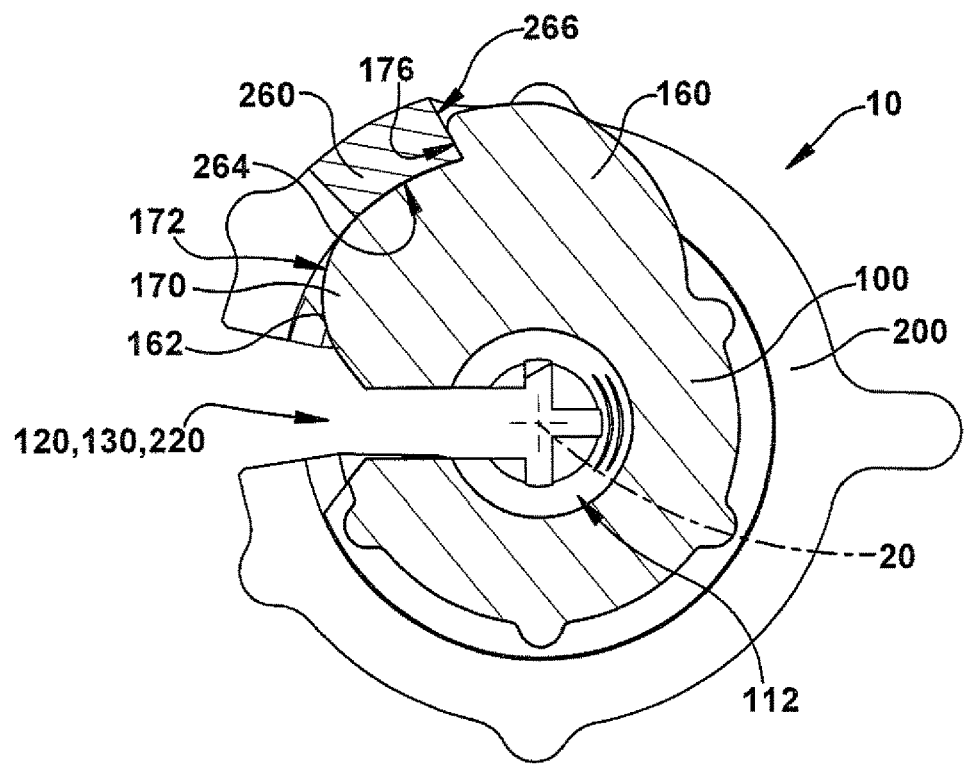

In an adjusting condition of the controller 10, the tab 260 cooperates with the element 160 to help maintain the cap 200 in an adjusting position that permits adjusting the axial position of the controller on the guidewire 50. This is illustrated in FIG. 11B. Referring to FIG. 11B, the adjusting position is reached when the lateral surface 266 of the tab 260 engages the surface 182 of the third portion 180 of the element 160. The engagement of these surfaces 266 and 182 results in resistance, albeit a relatively low resistance, to further rotation of the cap 200 relative to the housing 100. This relatively low resistance to further rotation conveniently allows for the cap 200 to be rotated further to the receiving condition with relative ease on the part of the user.

When the cap 200 is in the adjusting position, the cap blocks the primary receiving portion 130 of the slot 120 and therefore blocks removal of the guidewire 50 from the controller 10. When the cap 200 is in the adjusting position, the cap actuates the fingers 142 of the gripper 140 so as to release their grasp on the guidewire, thus permitting the guidewire 50 to slide with ease in the passage 112. When the controller 10 is adjusted to the desired axial position on the guidewire 50, the cap 200 can be tightened to actuate the fingers 142 and reestablish the grasp of the gripper 140 on the guidewire.

Advantageously, the cooperation between the tab 260 and the element 160 provides tactile indication that the controller 10 is in the adjusting condition. Additionally, in blocking rotational movement of the cap 200 at the adjusting position, the cap is prevented from inadvertent rotation beyond the adjusting position that would unblock the primary receiving portion 130 of the slot 120 and place the controller 10 in the receiving condition. Blocking inadvertently placing the controller 10 in the receiving condition prevents unintentionally disconnecting the controller from the guidewire 50.

Figure 10A:
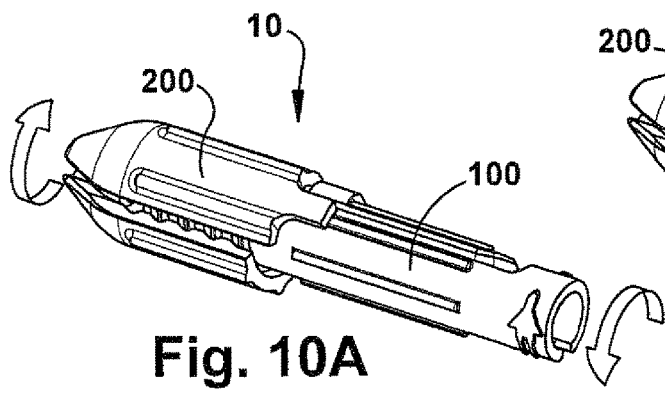
FIGS. 10A-10E are perspective views illustrating the operation of the control apparatus of FIGS. 1 and 2.

FIGS. 10A-10E illustrate the operation of the controller 10. Referring to FIG. 10A, the cap 200 and/or the housing 100 are rotated relative to each other, as indicated generally by the arrows by the arrows in FIG. 10A, in the direction of loosening the cap until the tactile response indicates that the controller 10 is in the receiving condition.

Figure 10B:
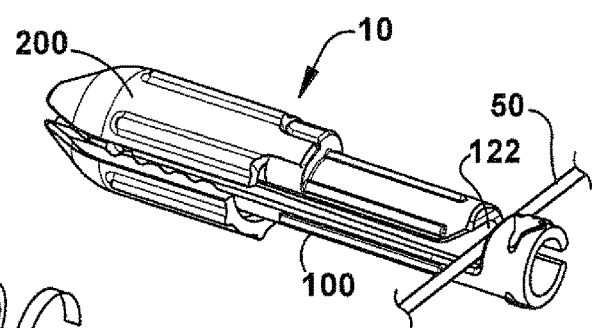

Next, as shown in FIG. 10B, the guidewire 50 is inserted into the receiving slot 122, as indicated generally by the arrows by the arrow in FIG. 10B. Positioning the guidewire 50 such that it is seated in the receiving slot 122 places the guidewire adjacent to, and extending transversely to, the primary and secondary receiving slots 130 and 132.

Figure 10C:
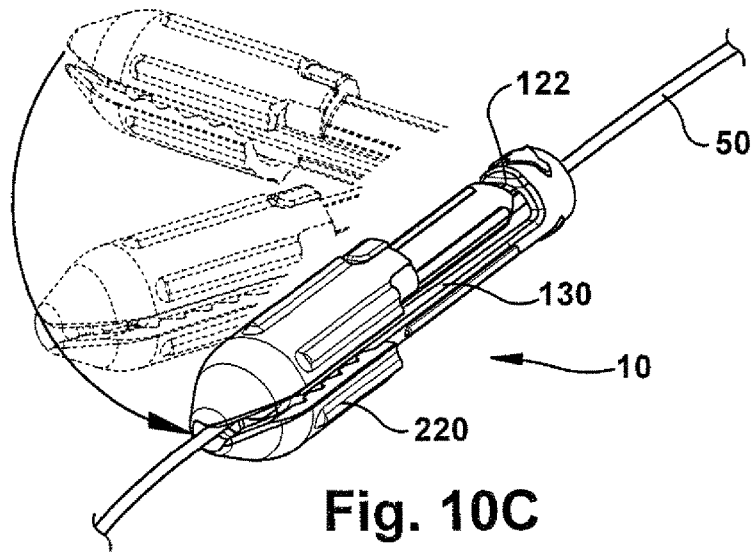

Next, as shown in FIG. 10C, the controller is pivoted, as indicated generally by the arrows by the arrow in FIG. 10C, so that the guidewire 50 enters the primary and secondary receiving slots 130 and 132. Since the controller 10 is in the receiving condition, the slot 220 in the cap is aligned with the primary receiving slot 130, thus facilitating entry of the guidewire. This positions the guidewire 50 in the passage 112, as shown in FIG. 10D.

Figure 10D:
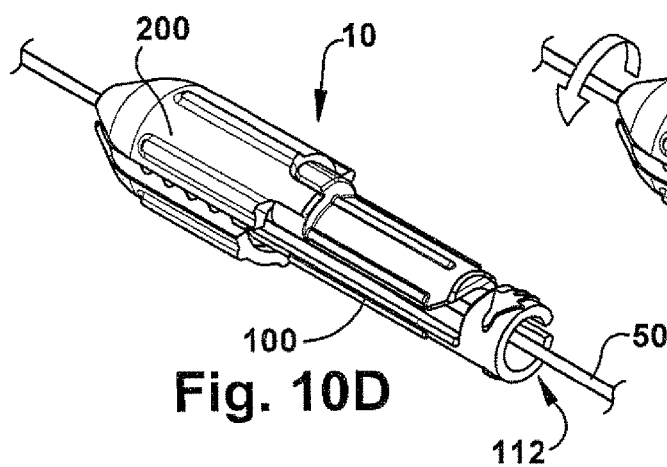

Next, referring to FIG. 10D, the controller 10 can be adjusted to the desired axial position on the guidewire, as indicated generally by the arrows in FIG. 10D. Prior to adjusting the axial position, the cap 200 could be rotated to place the controller 10 in the adjusting condition so as to prevent inadvertently removing the guidewire 50 from the passage 112.

Figure 10E:
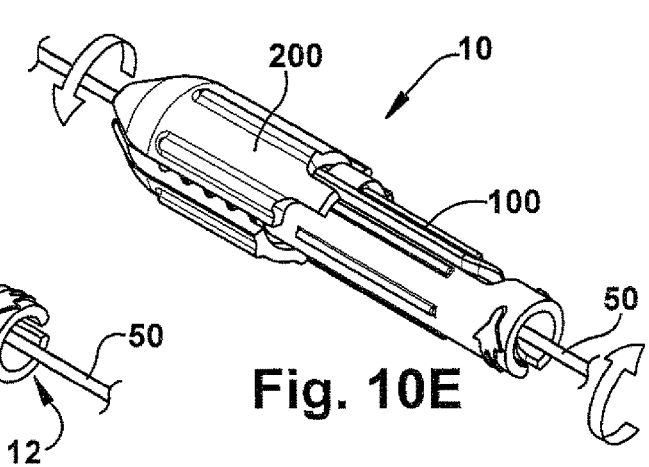

Next, as shown in FIG. 10E, the cap 200 and/or the housing 100 are rotated relative to each other, as indicated generally by the arrows in FIG. 10E, in the direction of tightening the cap until the controller 10 is tightly secured to the guidewire. If axial adjustment of the position of the controller 10 on the guidewire 50 is desired, the user simply unscrews the cap 200 until reaching the tactile indication that the controller has reached the adjusting condition, at which point the controller position can be adjusted and the cap re-tightened.

From the above description of the invention, those skilled in the art will perceive improvements, changes and modifications. Such improvements, changes and modifications within the skill of the art are intended to be covered by the appended claims.

Having described the invention, the following is claimed:

1. A controller for manually controlling a guidewire, the controller comprising:
   a housing comprising a passage for receiving the guidewire;
   a gripper that is actuatable to grasp the guidewire in the passage; and
   a cap connected to the housing by threads, the cap being rotatable relative to the housing so that the threads actuate the gripper, the housing comprising an element in addition to the threads for maintaining the cap in a receiving position, the cap when in the receiving position placing the controller in a condition in which the guidewire can be moved into and out of the passage.

2. The controller recited in claim 1, wherein the element comprises a first portion configured to maintain the cap in the receiving position.

3. The controller recited in claim 2, wherein the cap comprises a tab configured to engage the first portion of the element to maintain the cap in the receiving position.

4. The controller recited in claim 3, wherein the element projects outward from the housing and the tab projects axially from an end of the cap, an inward facing surface of the tab configured to engage an opposing outward facing surface of the first portion of the element to maintain the cap in the receiving position.

5. The controller recited in claim 4, wherein the engagement of the inward facing surface of the tab with the outward facing surface of the first portion of the element causes the tab to deflect, a resulting frictional engagement between the tab and the first portion of the element maintaining the cap in the receiving position.

6. The controller recited in claim 2, wherein the element comprises a second portion configured to block rotation of the cap to thereby prevent disconnection of the cap from the housing.

7. The controller recited in claim 6, wherein the cap comprises a tab configured to engage the second portion of the element to block rotation of the cap.

8. The controller recited in claim 7, wherein the element projects outward from the housing and the tab projects axially from an end of the cap, a lateral surface of the tab configured to engage an opposing lateral surface of the second portion of the element to block rotation of the cap.

9. The controller recited in claim 1, wherein the element comprises a third portion that inhibits rotation of the cap at an adjusting position, the axial position of the controller relative to the guidewire being adjustable when the cap is in the adjusting position.

10. The controller recited in claim 9, wherein the cap comprises a tab configured to engage the third portion of the element to inhibit rotation of the cap at the adjusting position.

11. The controller recited in claim 10, wherein the element projects radially outward from the housing and the tab projects axially from an end of the cap, a lateral surface of the tab configured to engage an opposing lateral surface of the third portion of the element is configured to inhibit rotation of the cap at the adjusting position.

12. The controller recited in claim 11, wherein the tab is deflectable outwardly with respect to the axis, the tab being responsive to a threshold degree of rotational force being applied to the cap to deflect and move over the lateral surface of the third portion and onto the second portion of the element.

13. The controller recited in claim 9, wherein the cap when in the adjusting position is configured to block removal of the guidewire from the passage.

14. The controller recited in claim 1, wherein the cap has a threaded connection with the housing, the threads of at least one of the housing and cap having asymmetrical flank angles that facilitate an initial connection of the cap to the housing by being configured to insert the housing axially into the cap without requiring rotation.

15. The controller recited in claim 14, wherein the threads of the housing have a lead flank angle that is greater than a rear flank angle of the housing threads.

16. The controller recited in claim 1, wherein the cap has a threaded connection with the housing, the cap being rotatable in a first direction to actuate the gripper to grasp the guidewire and in an opposite second direction to actuate the gripper to release the guidewire.

17. The controller recited in claim 16, wherein the gripper comprises collet fingers spaced radially about the passage, the fingers being deflectable radially inward to grasp the guidewire and radially outward to release the guidewire.

18. The controller recited in claim 17, wherein the collet fingers are configured to deflect radially inward in response to rotation of the cap in the first direction, and the collet fingers are configured to deflect radially outward in response to rotation of the cap in the second direction.

19. The controller recited in claim 18, wherein the collet fingers are spaced asymmetrically.

20. The controller recited in claim 19, wherein space between a first adjacent pair of fingers is greater than the space between remaining adjacent pairs of fingers, the space permitting insertion of the guidewire between the first adjacent pair, the space between the remaining adjacent pairs helping to position the guidewire in the passage until the gripper is actuated to grasp the guidewire.

21. The controller recited in claim 17, wherein the housing comprises a slot that provides guidewire access to the passage, a portion of the slot comprising space between an adjacent pair of the collet fingers.

22. The controller recited in claim 1, wherein the housing comprises a slot that provides guidewire access to the passage.

23. The controller recited in claim 22, wherein the slot comprises:
   an engagement portion that extends transverse to the axis;
   a primary receiving portion that extends parallel to the axis from a first end of the housing and intersects a first end of the engagement portion; and
   a secondary receiving portion that extends parallel to the axis from a second end of the housing and intersects a second end of the engagement portion.

24. The controller recited in claim 23, wherein the housing has a central longitudinal axis, the passage extending through the housing and being centered on the axis, the slot providing access to the passage along the entire length of the passage.

25. The controller recited in claim 23, wherein the primary and secondary receiving portions are positioned on radially opposite sides of the housing.

26. The controller recited in claim 23, wherein the engagement portion is adapted to initially receive the guidewire extending transverse to the axis, the housing and cap when in the receiving position being adapted to permit rotational maneuvering of the controller so that the guidewire is configured to enter the primary and secondary slots to thereby position the guidewire within the passage and extending substantially parallel to the axis.

27. The controller recited in claim 22, wherein the cap comprises a slot that is coextensive with the slot in the housing when the cap is in the receiving position.

28. The controller recited in claim 22, wherein the cap is configured to block access to the slot in the housing when the cap is not in the receiving position.

29. A controller for manually controlling a guidewire, the controller comprising:
   a housing comprising a passage for receiving the guidewire;
   a gripper that is actuatable to grasp the guidewire in the passage; and
   a cap connected to the housing, the cap being rotatable relative to the housing to actuate the gripper, the cap having a threaded connection with the housing, the threads of at least one of the housing and cap having asymmetrical flank angles that facilitate an initial connection of the cap to the housing by inserting the housing axially into the cap without requiring rotation.

* * * * *